US007107995B2

(12) United States Patent
Parkes (10) Patent No.: US 7,107,995 B2
(45) Date of Patent: Sep. 19, 2006

(54) URINARY-CONTROL DEVICE

(75) Inventor: Richard A. Parkes, Bloomfield Hills, MI (US)

(73) Assignee: C&L Medical Supply Corporation, Laurinburg, NC (US)

( * ) Notice: Subject to any disclaimer, the term of this patent is extended or adjusted under 35 U.S.C. 154(b) by 497 days.

(21) Appl. No.: 10/430,572

(22) Filed: May 6, 2003

(65) Prior Publication Data

US 2004/0129277 A1    Jul. 8, 2004

Related U.S. Application Data

(63) Continuation-in-part of application No. 10/316,719, filed on Dec. 11, 2002, now Pat. No. 6,843,253.

(51) Int. Cl.
*A61F 5/48* (2006.01)
(52) U.S. Cl. .......................................... 128/885; 600/38
(58) Field of Classification Search ........ 128/885–886, 128/DIG. 25; 285/305, 309, 415, 419; 403/310, 403/311, 313; 600/29–31, 38–40
See application file for complete search history.

(56) References Cited

U.S. PATENT DOCUMENTS

| 1,531,451 | A | | 3/1925 | Neal |
| 1,872,857 | A | | 8/1932 | Wesson et al. |
| 4,155,574 | A | * | 5/1979 | Hulsey ........................ 285/236 |
| 4,549,530 | A | | 10/1985 | Finney ........................ 128/1 R |
| 5,415,435 | A | * | 5/1995 | Colbert ........................ 285/23 |
| 5,571,125 | A | | 11/1996 | Chadwick .................... 606/157 |
| 5,729,872 | A | * | 3/1998 | Ginocchio .................... 24/16 R |
| 6,131,576 | A | * | 10/2000 | Davis .......................... 128/885 |
| 6,349,727 | B1 | | 2/2002 | Stewart, Jr. .................. 128/885 |
| 6,520,906 | B1 | * | 2/2003 | Yanagi ........................ 600/38 |
| 2002/0017303 | A1 | | 2/2002 | Single et al. ................ 128/848 |
| 2002/0111640 | A1 | | 8/2002 | Krause et al. ............... 606/151 |
| 2002/0153013 | A1 | | 10/2002 | Single et al. ................ 128/885 |
| 2002/0153014 | A1 | | 10/2002 | Cheng et al. ................ 128/885 |

\* cited by examiner

*Primary Examiner*—Michael A. Brown
(74) *Attorney, Agent, or Firm*—Bliss McGlynn, P.C.

(57) ABSTRACT

A urinary-control device for inhibiting male incontinence includes an upper clamping member; a lower clamping member; a hinge; and a releasable, self-locking mechanism. The upper clamping member has first and second distal ends and a substantially arcuate inner surface extending therebetween. The inner surface is adapted to be disposed about a portion of a penis. The lower clamping member has first and second distal ends and a substantially arcuate inner surface extending therebetween. The inner surface is adapted to be disposed about a portion of the penis and opposite the upper clamping member. The hinge is defined at the first distal ends for allowing articulated movement of the upper and lower clamping members relative to one another. The self-locking mechanism is defined at the second distal ends opposite the hinge and adapted to adjustably lock the second distal ends together, thereby mounting the device to the penis. The lower clamping member includes a removable pressure mechanism mounted on the inner surface of the lower clamping member and between the distal ends thereof so as to be located generally opposite the urethra of the penis. The removable pressure mechanism extends in a direction toward the inner surface of the upper clamping member so as to collapse the urethra in such a manner as to inhibit flow of urine therethrough when the device is mounted to the penis.

12 Claims, 5 Drawing Sheets

URINARY-CONTROL DEVICE

CROSS-REFERENCE TO A RELATED APPLICATION

This is a continuation-in-part application and claims benefit of U.S. patent application Ser. No. 10/316,719 filed on Dec. 11, 2002 now U.S. Pat. No. 6,843,253 and entitled "Urinary-Control Device."

BACKGROUND OF THE INVENTION

1. Field of the Invention

The present invention relates, generally, to a urinary-control device employed to combat male incontinence and, more particularly, to a urethra clamp.

2. Description of the Related Art

Incontinence—the uncontrolled and undesired passage of urine—is a problem faced by many men and, especially, older men. Incontinence may be caused by, for example, medical operations, partial or full sphincter loss, disease, neurological dysfunction, malformation of the urethral valve, and physical deterioration accompanying advancing age such that the natural urethral valve or sphincter is no longer capable of controlling the flow of urine from the bladder. Whatever the cause, incontinence is a significant problem resulting in distress, embarrassment, inconvenience, and restriction of activities.

It is known in the related art to prevent involuntary flow of urine in incontinent males by clamping the penis via particular devices that cause pressure to be applied upon the urethra, which, consequently, restricts flow of urine through the penis. Devices of this type are typically positioned about and tightened around the shaft of the penis until sufficient pressure is applied to the corpus spongiosum, in general, and the urethra, in particular, to substantially or completely close the urethra. Many of the devices known in the related art include a rigid or resilient projection that is positioned beneath the urethra and corpus spongiosum when mounted to the penis. The projection acts to apply the necessary pressure to clamp the urethra. The device is loosened or removed from the penis to permit flow of urine through the urethra when appropriate.

While clamping devices of the type known in the related art can create sufficient pressure to stop flow of involuntary urine to a penis of a particular size in a flaccid state, they suffer from the disadvantage in that they cannot create sufficient pressures to stop flow of involuntary urine to penises of various sizes in a flaccid state. More specifically, they cannot ensure that sufficient pressure is applied to the urethra and the corpus spongiosum of each of many penises of various sizes in a flaccid state to prevent or substantially reduce leakage from the urethra. They are not selectively and variably adjustable to enable application of different pressures to the urethra and the corpus spongiosum to accommodate needs of individual users. Leakage from the urethra caused by this inability of the clamping devices known in the related art is a major drawback of the urinary-control devices presently available on the market.

Clamping devices of the type known in the related art also suffer from the disadvantage in that they often reduce or stop blood flow through the penis. More specifically, while ensuring that sufficient pressure is applied to the urethra and the corpus spongiosum to prevent or substantially reduce leakage from the urethra, the devices apply undue pressure to the penile shaft. This unacceptable and sometimes painful amount of pressure is applied to tissues other than the urethra and corpus spongiosum. In particular, the devices apply undue pressure to a group of penile elements lying just below or close to the epidermal layer of the penis, including the superficial dorsal vein, superficial lateral veins, helicine arteriole, cavernosal artery, corpus cavernosum, tunica albuginea, superficial lateral vein, and emissary vein. This group will be referred to hereinafter as the neurovascular bundle. Unfortunately, excessive pressure applied to the neurovascular bundle can result in reduced blood flow through the penis and even necrosis of the penile tissue. Reduced blood flow caused by the clamping devices known in the related art is very uncomfortable and a major drawback of the urinary-control devices presently available on the market.

Urinary-control devices of the type known in the related art can also be difficult or cumbersome to properly position on the shaft of the penis. Some are difficult to release when the user voluntarily attempts to empty his bladder, causing undue delay and embarrassment. Still others suffer from the disadvantage that they are bulky and relatively heavy and, therefore, increase the discomfort associated with using these devices. Finally, while male urinary-control devices of the type known in the related art generally clamp the urethra so as to stop unwanted flow therethrough, they are uncomfortable to wear for extended periods of time.

Thus, there is a need in the related art for a urinary-control device for male incontinence that allows for delivery of different pressures to the urethra and the corpus spongiosum as a function of various sizes of penises in a flaccid state. More specifically, there remains a need in the related art for a urinary-control device employed to combat male incontinence that is selectively and variably adjustable to enable application of different pressures to the urethra and the corpus spongiosum to accommodate needs of individual users. There is a need in the related art for a urinary-control device that also allows for improved blood flow through the penis and is more convenient; easier to attach, remove, and use; and more comfortable than the clamping devices of the related art and relatively streamlined and lightweight. More specifically, there remains a need in the related art for a urinary-control device employed to combat male incontinence that uses a quick-release mechanism for one-handed operation so as to facilitate easy proper positioning on the penile shaft and removal therefrom for urination. There is a need in the related art for a urinary-control device that also is selectively and variably adjustable to enable application of different pressures to the penis to accommodate needs of individual users. There remains a need in the related art for a urinary-control device that also does not inflict pain, trauma, and/or damage to the neurovascular bundle so that the device may be comfortably worn by a user for extended periods of time without removal, except to permit urination. Finally, there is a need in the related art for a urinary-control device that also addresses all of the deficiencies of the known devices and is simple and inexpensive to construct.

SUMMARY OF THE INVENTION

The present invention overcomes the disadvantages in the related art in a urinary-control device employed to combat male incontinence. The device includes an upper clamping member, a lower clamping member, a hinge, and a releasable, self-locking mechanism. The upper clamping member has first and second distal ends and a substantially arcuate inner surface extending therebetween. The inner surface is adapted to be disposed about a portion of a penis. The lower clamping member has first and second distal ends and a substantially arcuate inner surface extending therebetween. The inner surface is adapted to be disposed about a portion of the penis and opposite the upper clamping member. The hinge is defined at the first distal ends for allowing articulated movement of the upper and lower clamping members relative to one another. The self-locking mechanism is defined at the second distal ends opposite the hinge and adapted to adjustably lock the second distal ends together, thereby mounting the device to the penis. The lower clamping member includes a removable pressure mechanism mounted on the inner surface of the lower clamping member and between the distal ends thereof so as to be located generally opposite the urethra of the penis. The removable pressure mechanism extends in a direction toward the inner surface of the upper clamping member so as to collapse the urethra in such a manner as to inhibit flow of urine therethrough when the device is mounted to the penis.

One advantage of the urinary-control device of the present invention is that it prevents or substantially reduces leakage from the urethra of penises of various sizes.

Another advantage of the urinary-control device of the present invention is that it allows for delivery of different pressures to the urethra and the corpus spongiosum as a function of various sizes of penises in a flaccid state.

Another advantage of the urinary-control device of the present invention is that it uses variable adjustment to enable application of different pressures to the urethra and the corpus spongiosum to accommodate needs of individual users.

Another advantage of the urinary-control device of the present invention is that it permits blood flow through the penis while preventing or substantially reducing leakage from the urethra.

Another advantage of the urinary-control device of the present invention is that it is more convenient and easier to attach, remove, and use than such devices known in the related art.

Another advantage of the urinary-control device of the present invention is that it is lightweight.

Another advantage of the urinary-control device of the present invention is that it employs a quick-release mechanism for easy positioning on the penile shaft and removal therefrom for urination. In addition, the quick-release mechanism facilitates one-handed operation of the urinary-control device.

Another advantage of the urinary-control device of the present invention is that it uses variable adjustment to enable application of different pressures to the penis to accommodate needs of individual users.

Another advantage of the urinary-control device of the present invention is that it does not inflict pain, trauma, and/or damage to the skin and underlying tissues of the penile shaft.

Still another advantage of the urinary-control device of the present invention is that it is more comfortably worn by the user than such devices known in the related art and, thus, gives the user more confidence and freedom of movement.

Still another advantage of the urinary-control device of the present invention is that it is compact in design and, thus, unobtrusive.

Still another advantage of the urinary-control device of the present invention is that it is simple and inexpensive to construct.

Still another advantage of the urinary-control device of the present invention is that it is dishwasher-safe and, thus, may be easily cleaned so that it remains sanitary.

Other objects, features, and advantages of the present invention will be readily appreciated as the same becomes better understood while reading the subsequent description taken in conjunction with the accompanying drawings.

DETAILED DESCRIPTION OF THE INVENTION

Referring now to the figures, where like numerals are used to designate like structure, one embodiment of a urinary-control device for inhibiting male incontinence is generally indicated at 10 in FIGS. 1–8D. As shown in FIGS. 1, 2, 8B, 8C, and 8D, the device 10 is adapted to be disposed in operative use about a penis, generally indicated at 12. The penis 12 includes a head 14; a shaft, generally indicated at 16, extending substantially longitudinally from an end of the head 14; an epidermal layer 18 covering the shaft 16; and a neurovascular bundle, generally indicated at 20, extending substantially longitudinally through the interior of the shaft 16 beneath the epidermal layer 18. For purposes of description only and not by way of limitation, the neurovascular bundle 20 may include the urethra 22, corpus spongiosum 24, superficial dorsal vein 26, subcutaneous dorsal vein 28, subcutaneous lateral veins 30, and superficial lateral veins 32. However, those having ordinary skill in the art will appreciate that the neurovascular bundle 20 of the penis 12 includes elements additional to those described and shown.

As shown throughout FIGS. 1–8D, the device 10 generally includes an upper clamping member, generally indicated at 34, a lower clamping member, generally indicated at 36, a hinge, generally indicated at 38, and a releasable, self-locking mechanism, generally indicated at 40. Each of the upper and lower clamping members 34, 36, respectively, hinge 38, and self-locking mechanism 40 is described in detail below.

Figure 1:
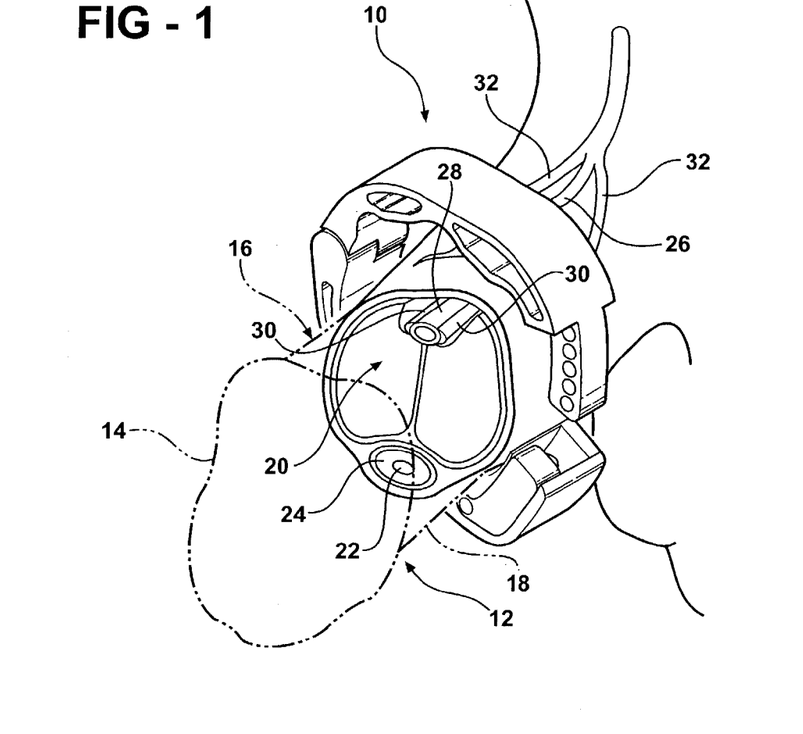
FIG. 1 is an environmental view of one embodiment of the urinary-control device of the present invention showing the neurovascular bundle of a penis and the device disposed in an open manner about the penis.
Figure 2:
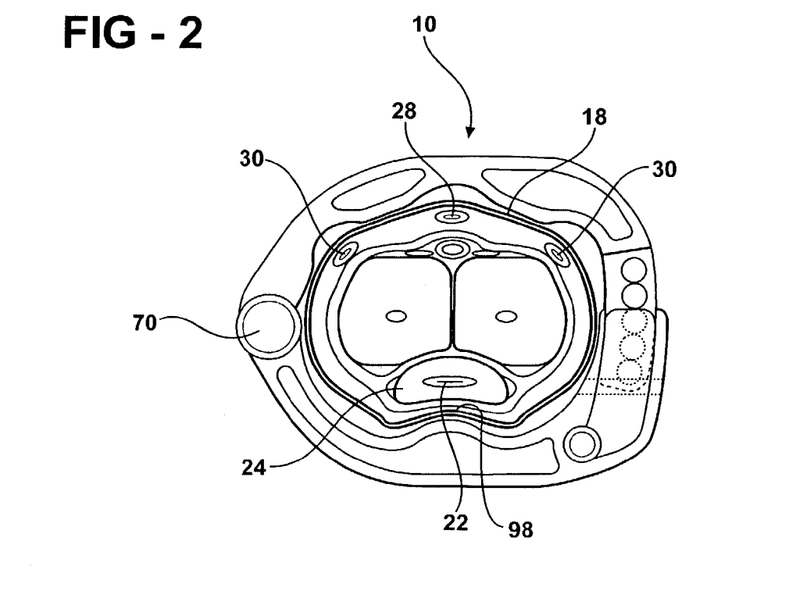
FIG. 2 is an elevational front view of the embodiment of the urinary-control device of the present invention illustrated in FIG. 1 showing a penis in cross-section and the device disposed in a closed manner about the penis.
Figures 3, 4, 5:
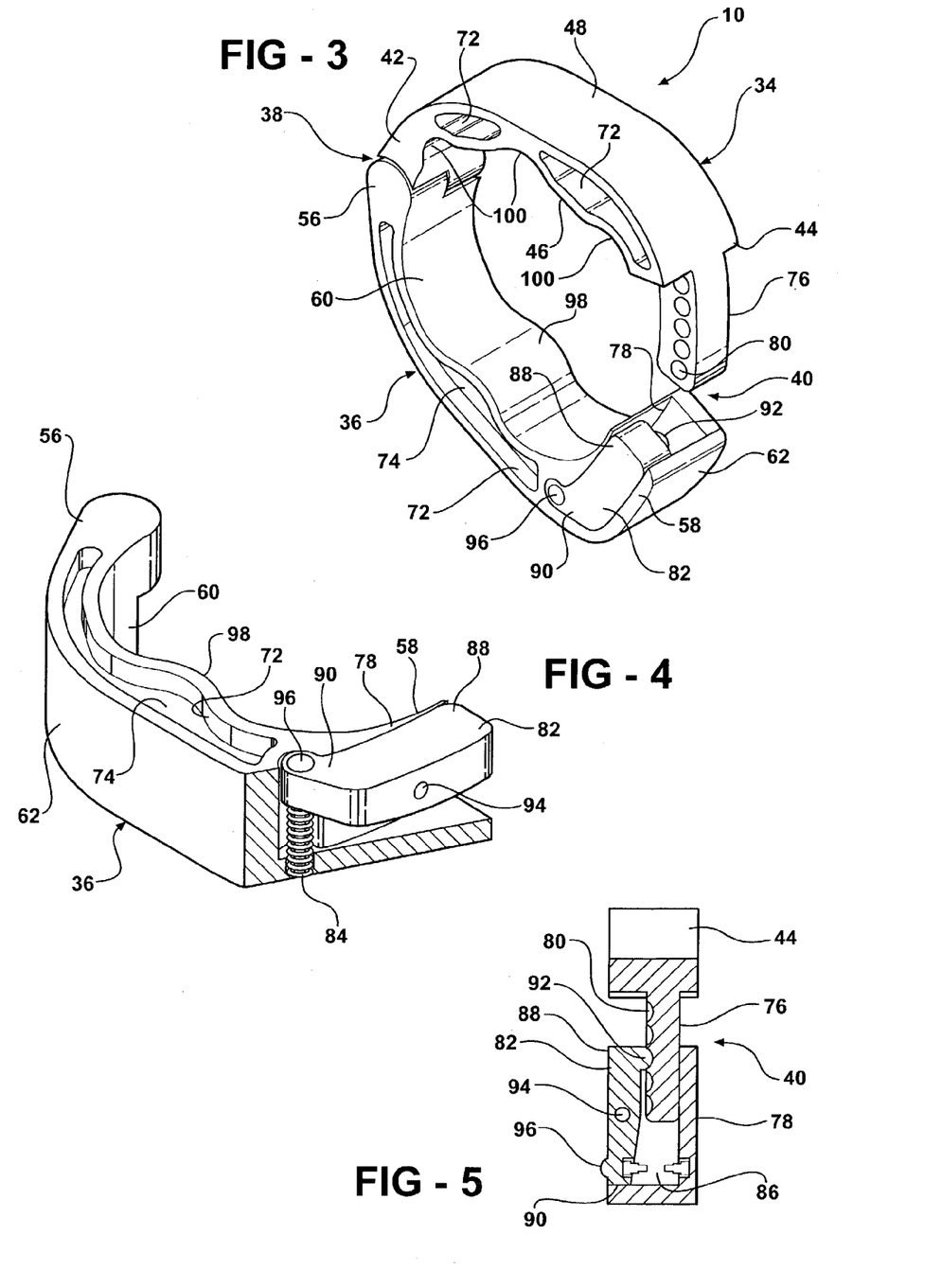
FIG. 3 is a first perspective view of the embodiment of the urinary-control device of the present invention illustrated in FIG. 1 showing the device in an open disposition.
FIG. 4 is a perspective view of the lower clamping member of the embodiment of the urinary-control device of the present invention illustrated in FIG. 1.
FIG. 5 is a cross-sectional view of the releasable, self-locking mechanism of the embodiment of the urinary-control device of the present invention illustrated in FIG. 1.
Figure 6:
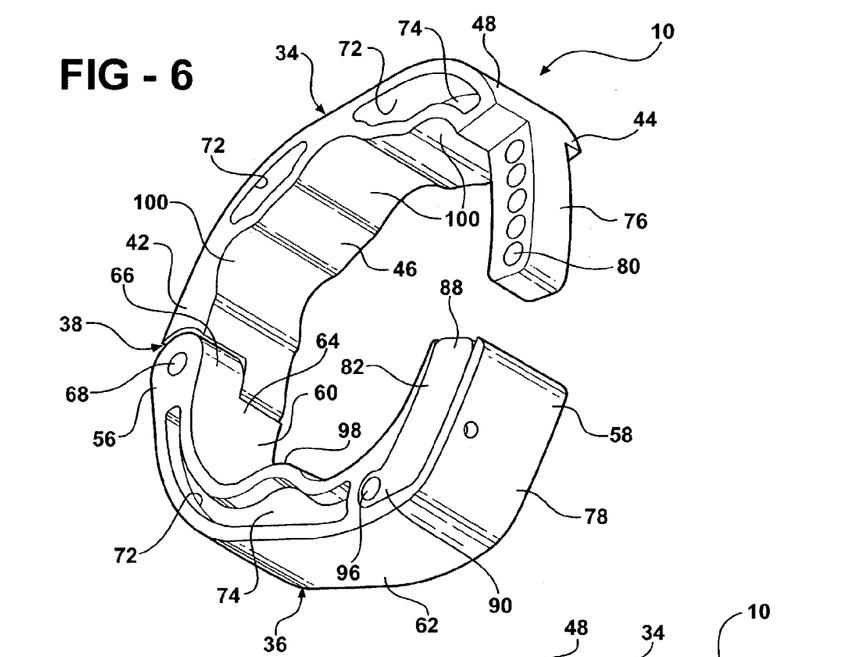
FIG. 6 is a second perspective view of the embodiment of the urinary-control device of the present invention illustrated in FIG. 1 showing the device in an open disposition.
Figure 7:
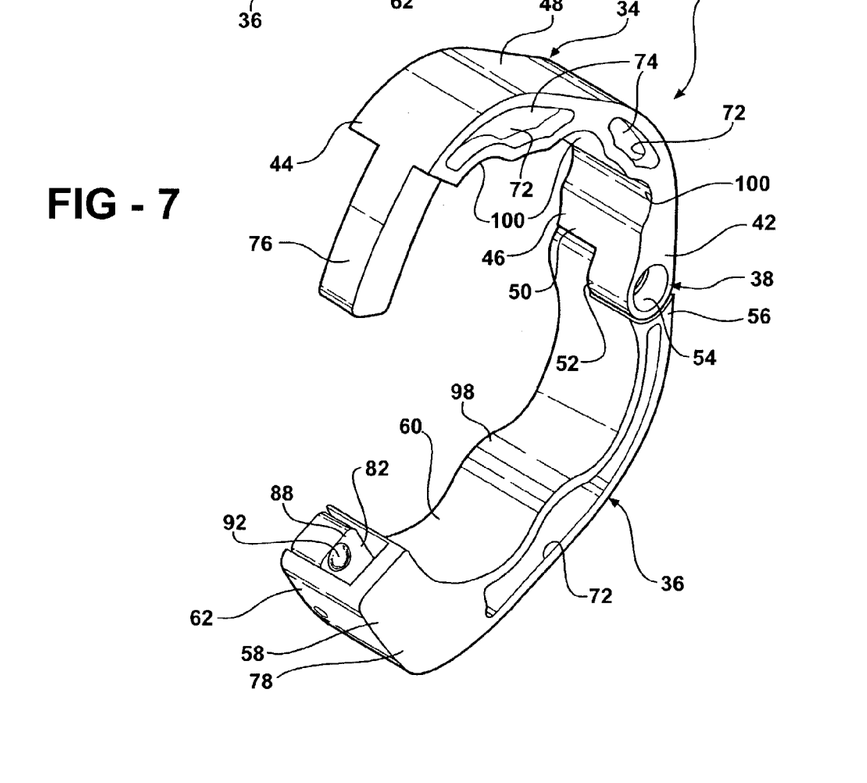
FIG. 7 is a third perspective view of the embodiment of the urinary-control device of the present invention illustrated in FIG. 1 showing the device in an open disposition.

As best shown in FIGS. 3, 6, and 7, the upper clamping member 34 has a first distal end 42, a second distal end 44, and a substantially arcuate inner surface 46 extending between the first and second distal ends 42, 44, respectively. The inner surface 46 is adapted to be disposed about a portion of the penis 12. More particularly, the inner surface 46 is adapted to be disposed about substantially the top hemisphere of the penis 12 and is substantially non-linear, as described in greater detail below.

The upper clamping member 34 has also a substantially arcuate outer surface 48 extending between the first and second distal ends 42, 44, respectively. Preferably, a portion of the outer surface 48 is substantially flat. Also, the upper clamping member 34 has a substantially uniform width and non-uniform thickness. The terminal end of distal end 44 defines a portion of the self-locking mechanism 40, which is described in detail below. Further, as shown in FIG. 7, one half 50 of distal end 42 is substantially uniformly concave, and the other half 52 of distal end 42 is substantially uniformly convex. Half 52 extends farther than half 50 and has a hole 54 formed through the width of half 52.

As best shown in FIGS. 3, 4, 6, and 7, the lower clamping member 36 has a first distal end 56, a second distal end 58, and a substantially arcuate inner surface 60 extending between the first and second distal ends 56, 58, respectively. The inner surface 60 is adapted to be disposed about a portion of the penis 12 and opposite the upper clamping member 34. More particularly, the inner surface 60 is adapted to be disposed about substantially the bottom hemisphere of the penis 12 and is substantially non-linear, as described in greater detail below.

As best shown in FIG. 6, the lower clamping member 36 also has a substantially arcuate outer surface 62 extending between the first and second distal ends 56, 58, respectively. Preferably, a portion of the outer surface 62 is substantially flat. Also, the lower clamping member 36 has a substantially uniform width and non-uniform thickness. Distal end 58 defines a portion of the self-locking mechanism 40, which is described in detail below. Further, as shown in FIG. 6, one half 64 of distal end 56 is substantially uniformly concave, and the other half 66 of distal end 56 is substantially uniformly convex. A hole 68 is formed through the width of half 66, which extends farther than half 64. Thus, as best shown in FIG. 7, the concave and convex halves 50, 52, respectively, of distal end 42 of the upper clamping member 34 are adapted to matingly engage the convex and concave halves 66, 64 of distal end 56 of the lower clamping member 36.

Those having ordinary skill in the art will appreciate that the upper and lower clamping members 34, 36, respectively, can have any suitable shape. More particularly, those having ordinary skill in the art will appreciate that the inner surfaces 46, 60, outer surfaces 48, 62, and distal ends 42, 44, 56, 58 can have any suitable shape and structural relationship with respect to each other.

As shown throughout FIGS. 1–8D, the hinge 38 is defined at the corresponding first distal ends 42, 56 of the upper and lower clamping members 34, 36, respectively, for allowing articulated movement of the upper and lower clamping members 34, 36, respectively, relative to one another. Preferably, the hinge 38, as shown in FIGS. 2, 8A, 8B, 8C, and 8D, includes a pin 70, for example, that extends through the holes 54, 68 of the convex halves 52, 66, respectively, of distal end 42 of the upper clamping member 34 and distal end 56 of the lower clamping member 36, respectively, for allowing articulated movement of the upper and lower clamping members 34, 36, respectively, relative to one another. However, those having ordinary skill in the art will appreciate that any suitable hinge can be used in the device 10 for allowing articulated movement of the upper and lower clamping members 34, 36, respectively, relative to one another.

Preferably and as best shown in FIGS. 3, 4, 6, and 7, each of the upper and lower clamping members 34, 36, respectively, includes at least one cavity 72 extending for a substantial portion of the width of the upper clamping member 34 or the lower clamping member 36. The cavities 72 act to reduce the weight of the device 10. Each of the cavities 72 has an upper surface and a lower surface and can have a stiffening web 74 extending therebetween. The web 74 facilitates reduced weight, but provides structural integrity to the device 10 and insures that the upper and lower surfaces of the cavity 72 do not flex.

Referring now to FIGS. 4, 6, 7, and 8A, the upper clamping member 34 may include a plurality of cavities 72. More specifically, the upper clamping member 34 may include two closed cavities 72 of different sizes and shapes, disposed substantially equidistantly from the center of the upper clamping member 34, and, together, extending a substantial length of the upper clamping member 34. The lower clamping member 36 includes one closed cavity 72 extending a substantial length of the lower clamping member 36 and having a different shape and longer than each of the cavities 72 of the upper clamping member 34. Each cavity is bisected by a web 74.

Those having ordinary skill in the art will appreciate that each of the upper and lower clamping members 34, 36, respectively, can include any sufficient number of cavities 72 for reducing the weight of the device 10. Those having ordinary skill in the art will appreciate also that each of the cavities 72 can have any suitable shape and extend for a suitable portion of the width, length, and depth of the upper clamping member 34 or the lower clamping member 36. Furthermore, those having ordinary skill in the art will appreciate also that the cavities 72 can have any suitable structural relationship with respect to each other.

As shown throughout FIGS. 1–8D, the self-locking mechanism 40 is defined at the corresponding second distal ends 44, 58 of the upper and lower clamping members 34, 36, respectively, opposite the hinge 38 and adapted to adjustably lock the second distal ends 44, 58 together, thereby mounting the device 10 to the penis 12. Preferably and as best shown in FIGS. 3, 4, 5, 6, and 7, the self-locking mechanism 40 includes a male member 76 and a female member 78. The male member 76 is defined at distal end 44 of the upper clamping member 34 and may include a substantially rectangular shape in cross-section. The male member 76 extends longitudinally from the remainder of the upper clamping member 34. The male member 76 has a reduced width with respect to the rest of the upper clamping member 34. The male member 76 is also cooperatively and adjustably received within the female member 78 and includes a plurality of detents 80 formed along the length of the male member 76. Preferably, the male member 76 includes five longitudinally aligned detents 80, which extend into the width of the male member 76 and permit five incremental locking positions for the device 10. However, those having ordinary skill in the art will appreciate that the male member 76 may include any number of detents 80 that is suitable for the intended purpose.

The female member 78 is defined at distal end 58 of the lower clamping member 36 and is co-extensive with the remainder of the lower clamping member 36. The female member 78 is shaped to complementarily receive the male member 76. The female member 78 also includes a latching member 82 and a biasing member 84 that acts to bias the latching member 82 into engagement with at least one of the detents 80 to allow the upper and lower clamping members 34, 36, respectively, to be adjustably mounted to the penis 12. Preferably, the biasing member 84 may include a lock spring 84 that is adapted to be disposed in a spring pocket 86, as shown in FIG. 5.

As illustrated in FIGS. 3–7, the latching member 82 includes a pair of distal ends 88, 90 and a pawl portion 92 formed proximate to distal end 88. The biasing member 84 acts on the latching member 82 proximate distal end 90, which is disposed spaced from the pawl portion 92. More specifically, the biasing member 84 acts to bias the latching member 82 about a pivot axis defined by a pin 94 so that the pawl portion 92 is forced into engagement with one of the detents 80. The latching member 82 is pivotable about the pin 94 disposed between the pawl portion 92 and the biasing member 84 in response to a force acting in a direction opposite the biasing force generated by the biasing member 84 to pivot the pawl portion 92 out of engagement with one of the detents 80. Activating a release-lock button 96 causes the biasing member 84 to compress and the latching member 82 to pivot about the pin 94.

As best shown in FIGS. 3, 4, 6, and 7, the lower clamping member 36 includes a protrusion 98 formed on the inner surface 60 and between the first and second distal ends 56, 58, respectively, of the lower clamping member 36. The protrusion 98 is adapted to be located generally opposite the urethra 22 of the penis 12. The protrusion 98 extends in a direction toward the inner surface 46 of the upper clamping member 34 to collapse the urethra 22 in such a manner as to inhibit the flow of urine through the urethra 22 when the device 10 is mounted to the penis 12. Preferably, the protrusion 98 extends the entire width of the inner surface 60 and in a direction toward the inner surface 46 of the upper clamping member 34.

As best shown in FIGS. 3, 6, and 7, the upper clamping member 34 includes at least one vein-relief portion 100 formed on the inner surface 46 of the upper clamping member 34. Generally speaking, the vein-relief portion 100 is disposed opposite the neurovascular bundle 20 in the penis 12 such that the device 10 does not constrict blood flow through the neurovascular bundle 20 when the device 10 is mounted to the penis 12 even though the urethra 22 is effectively clamped. The vein-relief portion 100 is defined by an arcuate, shallow groove formed on the inner surface 46 of the upper clamping member 34 and opening in the general direction of the protrusion 98 formed on the inner surface 60 of the lower clamping member 36. The vein-relief portion 100 extends for the entire width of the upper clamping member 34.

Preferably, the upper clamping member 34 includes a plurality of vein-relief portions 100 disposed spaced relative to one another on the inner surface 46 of the upper clamping member 34. More specifically, the plurality of vein-relief portions 100 include a pair of lateral vein-relief portions 100 disposed spaced from one another and corresponding to the subcutaneous lateral veins 30 extending through the penis 12 as well as a dorsal vein-relief portion 100 disposed between the pair of lateral vein-relief portions 100. The dorsal vein-relief portion 100 corresponds to the subcutaneous dorsal vein 28 extending through the penis 12.

The upper and lower clamping members 34, 36, respectively, are made preferably from a durable and resilient plastic in a die-cast operation. The lock spring 84 is made preferably from a durable stainless steel, and the hinge pin 70 is made preferably from brass, stainless steel, or a brass-plated steel material.

Referring now to FIGS. 9–13B, an alternate embodiment of the urinary-control device for inhibiting male incontinence of the present invention is generally indicated at 110, where like numerals increased by 100 are used to designate like structure with respect to the device 10 illustrated in FIGS. 1–8D. Like the device 10, the device 110 is adapted to be disposed in operative use about a penis 12 in the manner generally depicted in FIGS. 1, 2, 8B, 8C, and 8D.

As shown throughout FIGS. 9–13B, the device 110 includes an upper clamping member, generally indicated at 134, a lower clamping member, generally indicated at 136, a hinge, generally indicated at 138, and a release mechanism, generally indicated at 140. Each of the upper and lower clamping members 134, 136, respectively, hinge 138, and release mechanism 140 is described in detail below.

Figure 9:
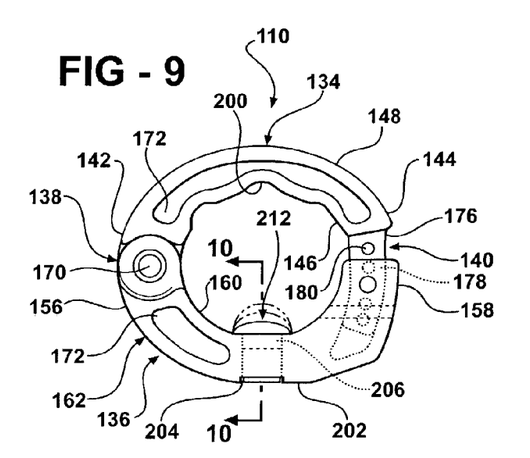
FIG. 9 is an elevational front view of another embodiment of the urinary-control device of the present invention showing the device in a closed disposition, illustrating various sizes of the removable pressure mechanisms thereof.

Referring specifically to FIG. 9, the upper clamping member 134 has a first distal end 142, a second distal end 144, and a substantially arcuate inner surface 146 extending between the first and second distal ends 142, 144, respectively. The inner surface 146 is adapted to be disposed about a portion of the penis 12. More particularly, the inner surface 146 is adapted to be disposed about substantially the top hemisphere of the penis 12 and is substantially non-linear, as described in greater detail below.

The upper clamping member 134 has also a substantially arcuate outer surface 148 extending between the first and second distal ends 142, 144, respectively. The terminal end of distal end 144 defines a portion of the self-locking mechanism 140, which is described in detail below. Further, like the embodiment illustrated in FIGS. 1–8, one half of distal end 142 is substantially uniformly concave, and the other half of distal end 142 is substantially uniformly convex. The one half extends farther than the other half and has a hole formed through the width of the one half.

Figure 11:
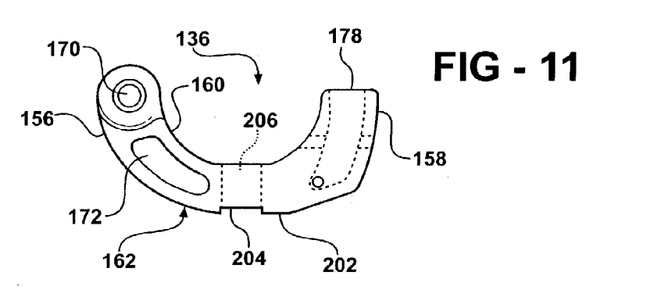
FIG. 11 is an elevational front view of the lower clamping member of the embodiment of the urinary-control device of the present invention illustrated in FIG. 9 showing the pressure mechanism removed from the lower clamping member.
Figure 12A:
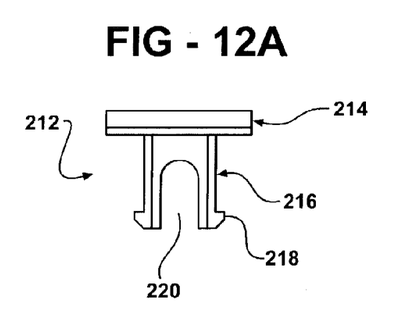
FIG. 12A is an elevational front view of the removable pressure mechanism of the urinary-control device illustrated in FIG. 9 having a first size.
Figure 12B:
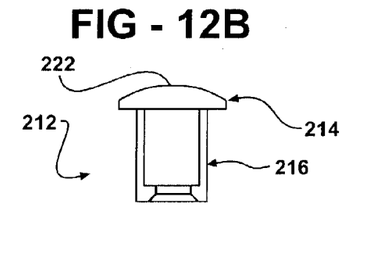
FIG. 12B is an end view of the removable pressure mechanism illustrated in FIG. 12A.
Figure 13A:
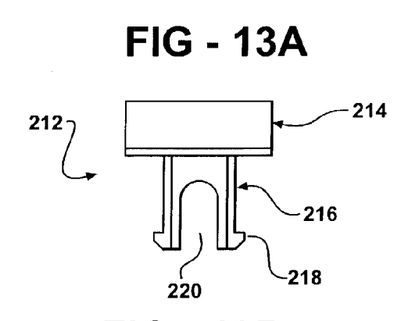
FIG. 13A is an elevational front view of the removable pressure mechanism of the urinary-control device illustrated in FIG. 9 having a second size greater than the first size shown in FIG. 12A.
Figure 13B:
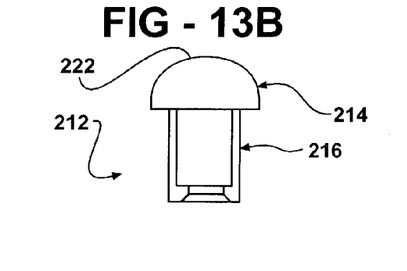
FIG. 13B is an end view of the removable pressure mechanism illustrated in FIG. 13A.

As shown in FIGS. 9 and 11, the lower clamping member 136 has a first distal end 156, a second distal end 158, and a substantially arcuate inner surface 160 extending between the first and second distal ends 156, 158, respectively. The inner surface 160 is adapted to be disposed about a portion of the penis 12 and opposite the upper clamping member

134. More particularly, the inner surface 160 is adapted to be disposed about substantially the bottom hemisphere of the penis 12 and is substantially non-linear, as described in greater detail below.

The lower clamping member 136 also has a substantially arcuate outer surface, generally indicated at 162, extending between the first and second distal ends 156, 158, respectively. Preferably, a substantially central portion 202 of the outer surface 162 is substantially flat and defines a perimeter surface 204, as shown also in FIG. 10, indented from the substantially flat central portion 202. More specifically, the entire area of the perimeter surface 204 is substantially flat and uniform and indented a substantially uniform distance from the substantially flat central portion 202.

Figure 10:
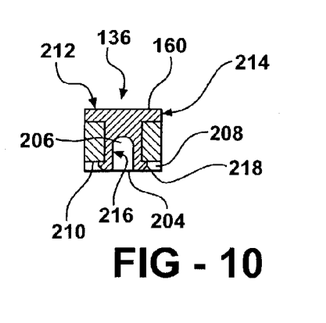
FIG. 10 is an cross-sectional view taken substantially along line "10—10" of FIG. 9 showing the removable pressure mechanism disposed in slots of the lower clamping member.

Preferably and still referring to FIGS. 9, 10, and 11, the lower clamping member 136 defines an aperture 206 disposed completely through the thickness of the substantially central portion 202 of the lower clamping member 136. More specifically, the aperture 206 extends from the perimeter surface 204 to the inner surface 160 of the lower clamping member 136. As best shown in FIG. 10, the lower clamping member 136 further includes at least one, but preferably a pair of slots 208 formed therein. Each slot 208 is defined longitudinally adjacent the aperture 206. Each slot 208 defines a bearing surface 210 on the lower clamping member 136. The function of each of the aperture 206, slot 208, and bearing surface 210 is described in detail below.

The distal end 158 of the lower clamping member 136 defines a portion of the release mechanism 140, which is described in detail below. Further, like the embodiment illustrated in FIGS. 1–8, one half of distal end 156 is substantially uniformly concave, and the other half of distal end 156 is substantially uniformly convex. A hole is formed through the width of the other half, which extends farther than the one half. Thus, the concave and convex halves of distal end 142 of the upper clamping member 134 are adapted to matingly engage the convex and concave halves of distal end 156 of the lower clamping member 136.

Those having ordinary skill in the art will appreciate that the upper and lower clamping members 134, 136, respectively, can have any suitable shape. More particularly, those having ordinary skill in the art will appreciate that the inner surfaces 146, 160, outer surfaces 148, 162, and distal ends 142, 144, 156, 158 can have any suitable shape and structural relationship with respect to each other.

As shown in FIG. 9, the hinge 138 is defined at the corresponding first distal ends 142, 156 of the upper and lower clamping members 134, 136, respectively, for allowing articulated movement of the upper and lower clamping members 134, 136, respectively, relative to one another. Preferably, the hinge 138 includes a pin 170, for example, that extends through the holes of the convex halves of distal end 142 of the upper clamping member 134 and distal end 156 of the lower clamping member 136, respectively, for allowing articulated movement of the upper and lower clamping members 134, 136, respectively, relative to one another. However, those having ordinary skill in the art will appreciate that any suitable hinge can be used in the device 110 for allowing articulated movement of the upper and lower clamping members 134, 136, respectively, relative to one another.

As shown in FIGS. 9 and 11, each of the upper and lower clamping members 134, 136, respectively, may include at least one cavity 172 extending for a substantial portion of the width of the upper clamping member 134 or the lower clamping member 136. The cavities 172 act to reduce the weight of the device 110. Each of the cavities 172 has an upper surface and a lower surface and can have a stiffening web extending therebetween. The web facilitates reduced weight, but provides structural integrity to the device 110 and insures that the upper and lower surfaces of the cavity 172 do not flex.

Preferably, the upper clamping member 134 includes one cavity 172 extending a substantial length of the upper clamping member 134. The lower clamping member 136 includes one cavity 172 disposed proximate distal end 156 of the lower clamping member 136 and having a different shape and shorter than the cavity 172 of the upper clamping member 134. Each cavity is bisected by a web. Those having ordinary skill in the art will appreciate that each of the upper and lower clamping members 134, 136, can include any sufficient number of cavities 172 for reducing the weight of the device 110. Furthermore, each of the cavities 172 can have any suitable shape and extend for a suitable portion of the width, length, and depth of the upper clamping member 134 or the lower clamping member 136. Those having ordinary skill in the art will also appreciate that the cavities 172 can have any suitable structural relationship with respect to each other.

As shown in FIG. 9, the release mechanism 140 is defined at the corresponding second distal ends 144, 158 of the upper and lower clamping members 134, 136, respectively, opposite the hinge 138 and adapted to adjustably lock the second distal ends 144, 158 together, thereby mounting the device 110 to the penis 12. Preferably, the release mechanism 140 includes a male member 176 and a female member 178. The male member 176 is defined at distal end 144 of the upper clamping member 134 and may include a substantially rectangular shape in cross-section. The male member 176 extends longitudinally from the remainder of the upper clamping member 134. The male member 176 has a reduced width with respect to the rest of the upper clamping member 134. The male member 176 is also cooperatively and adjustably received within the female member 178 and includes a plurality of detents 180 formed along the length of the male member 176. Preferably, the male member 176 includes five longitudinally aligned detents 180, which extend into the width of the male member 176 and permit five incremental locking positions for the device 110. However, those having ordinary skill in the art will appreciate that the male member 176 may include any number of detents 180 that is suitable for the intended purpose.

The female member 178 is defined at distal end 158 of the lower clamping member 136 and is co-extensive with the remainder of the lower clamping member 136. The female member 178 is shaped to complementarily receive the male member 176. The female member 178 also includes a latching member and a biasing member that acts to bias the latching member into engagement with at least one of the detents 180 to allow the upper and lower clamping members 134, 136, respectively, to be adjustably mounted to the penis 12. Preferably, the biasing member may include a lock spring that is adapted to be disposed in a spring pocket (not shown).

In the preferred embodiment, the release mechanism 140 is self-locking. Thus, like the embodiment illustrated in FIGS. 1–8, the latching member includes a pair of distal ends and a pawl portion formed proximate to distal end. The biasing member acts on the latching member proximate distal end, which is disposed spaced from the pawl portion. More specifically, the biasing member acts to bias the latching member about a pivot axis defined by a pin (not shown) so that the pawl portion is forced into engagement with one of the detents. The latching member is pivotable about the pin disposed between the pawl portion and the biasing member in response to a force acting in a direction opposite the biasing force generated by the biasing member to pivot the pawl portion out of engagement with one of the detents 180. Activating a release-lock button (not shown) causes the biasing member to compress and the latching member to pivot about the pin.

As shown in FIG. 9, the lower clamping member 136 includes a removable pressure mechanism, generally indicated at 212, formed on the inner surface 160 and between the first and second distal ends 156, 158, respectively, of the lower clamping member 136. The pressure mechanism 212 is removably insertable within the aperture 206 and is adapted to be located generally opposite the urethra 22 of the penis 12 in the same manner as illustrated in FIGS. 1, 2, 8B, 8C, and 8D. The removable pressure mechanism 212 extends in a direction toward the inner surface 146 of the upper clamping member 134 to collapse the urethra 22 in such a manner as to inhibit flow of urine through the urethra 22 when the device 110 is mounted to the penis 12. Preferably, the removable pressure mechanism 212 fills substantially the entire volume defined by the aperture 206 and extends in a direction toward the inner surface 146 of the upper clamping member 134.

Referring now to FIGS. 10 and 12A–13B, the removable pressure mechanism 212 includes a body, generally indicated at 214, and at least one leg, generally indicated at 216, extending from the body 214 and adapted to be received in a corresponding slot 208 of the lower clamping member 136 in snap-fit fashion. In the preferred embodiment depicted in these figures, the pressure mechanism 212 includes a pair of legs 216 extending in cantilevered fashion from the body 214. Each leg 216 has a foot portion 218 that extends outwardly and opposite the body 214. Each foot portion 218 is adapted to be received in a corresponding slot 208 in snap-fit fashion and bear against the bearing surface 210 of the lower clamping member 136. The pair of slots 208 are formed substantially opposite each other with respect to the aperture 206, and the pair of legs 216 are integrally connected proximate the body 214 and define an inverted substantially U-shaped space 220 therebetween.

The body 214 includes an upper portion 222 that defines a protrusion adapted to be located generally opposite the urethra 22. Thus, the upper portion 222 extends in a direction toward the inner surface 146 of the upper clamping member 134 so as to collapse the urethra 22 in such a manner as to inhibit flow of urine therethrough when the device 110 is mounted to the penis 12. More specifically, the upper portion 222 is of a substantially hemispherical shape such that the arcuate surface of the protrusion is adapted to be located generally opposite the urethra 22 and the substantially flat surface of the upper portion 222 is adapted to bear against the inner surface 160 of the lower clamping member 136.

Because the pressure mechanism 212 is removable, the urinary control device 110 of the present invention may be supplied with a number of mechanisms 212 having bodies 214 with upper portions 222 of different sizes. This allows for the delivery of different pressures to the urethra 22 as a function of various sizes of penises 12 in the flaccid state. FIG. 9 illustrates this flexibility using phantom lines to define the upper portion 222 of different sizes. Thus, the upper portions 222 of the various pressure mechanisms 212 extend toward the inner surface 146 of the upper clamping member 134 to varying degrees. FIGS. 12A–13B illustrate two examples of pressure mechanisms 212 that include upper portions 222 of different sizes. In one preferred embodiment illustrated in these figures, the upper portion 222 defines a substantially arcuate surface that is adapted to be located generally opposite the urethra 22. More specifically, by inserting a pressure mechanism 212 having a properly sized upper portion 222 into the aperture 206, the pressure mechanism 212 is selectively and variably adjustable to enable application of different pressures to the urethra 22 to accommodate needs of individual users of the removable pressure mechanism 212.

Those having ordinary skill in the art will appreciate that the perimeter surface 204, aperture 206, slot 208, bearing surface 210 and upper portion 222 can have any suitable shape, size, location, and structural relationship with respect to one another such that the removable pressure mechanism 212 can be selectively and variably adjustable to enable application of different pressures to the urethra 22 to accommodate needs of individual users of the removable pressure mechanism 212.

As shown in FIG. 9, the upper clamping member 134 includes at least one vein-relief portion 200 formed on the inner surface 146 of the upper clamping member 134. Generally speaking, the vein-relief portion 200 is disposed opposite the neurovascular bundle 20 in the penis 12 (FIG. 1) such that the device 110 does not constrict blood flow through the neurovascular bundle 20 when the device 110 is mounted to the penis 12 even though the urethra 22 is effectively clamped. The vein-relief portion 200 is defined by an arcuate, shallow groove formed on the inner surface 146 of the upper clamping member 134 and opening in the general direction of the removable pressure mechanism 212 formed on the inner surface 160 of the lower clamping member 136. The vein-relief portion 200 extends for the entire width of the upper clamping member 134.

Preferably, the upper clamping member 134 includes a plurality of vein-relief portions 200 disposed spaced relative to one another on the inner surface 146 of the upper clamping member 134. More specifically, the plurality of vein-relief portions 200 include a pair of lateral vein-relief portions 200 disposed spaced from one another and corresponding to the subcutaneous lateral veins 30 (FIGS. 1, 2, 8B, 8C, and 8D) extending through the penis 12 as well as a dorsal vein-relief portion 200 disposed between the pair of lateral vein-relief portions 200. The dorsal vein-relief portion 200 corresponds to the subcutaneous dorsal vein 28 (FIGS. 1, 2, 8B, 8C, and 8D) extending through the penis 12.

The upper and lower clamping members 134, 136, respectively, are made preferably from a durable and resilient plastic in a die-cast operation. The lock spring is made preferably from a durable stainless steel, and the hinge pin is made preferably from brass, stainless steel, or a brass-plated steel material. The device 110 may also be made in various sizes to accommodate penises of various sizes.

Figures 8A, 8B, 8C, 8D:
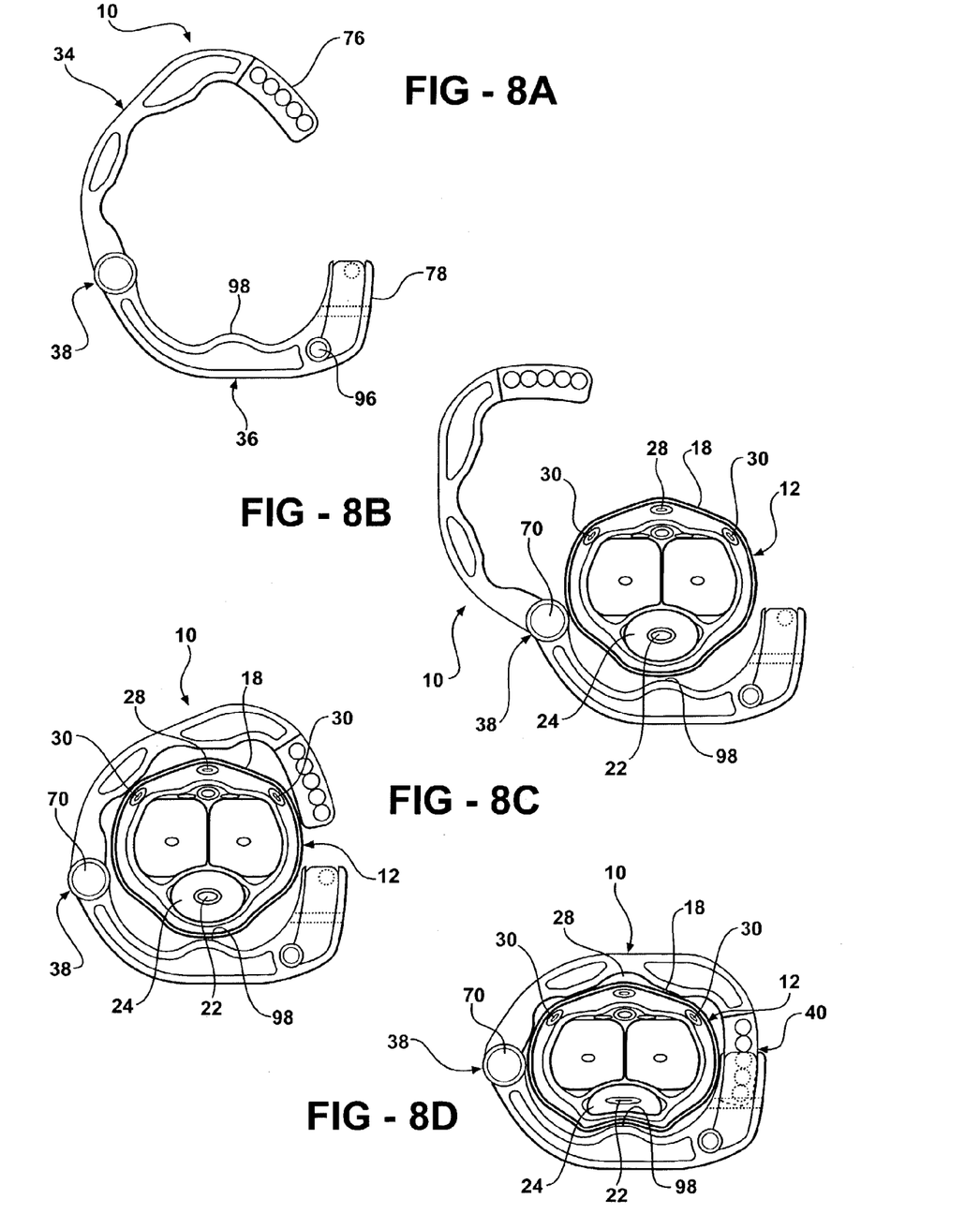
FIG. 8A is an elevational front view of the embodiment of the urinary-control device of the present invention illustrated in FIG. 1 showing the device in an open disposition.
FIGS. 8B–8D are a sequence of elevational front views of the embodiment of the urinary-control device of the present invention illustrated in FIG. 1 showing a penis in cross-section and the device disposed closing about the penis.

The user of the device 110 inserts a removable pressure mechanism 212 having a properly sized upper portion 222 into the aperture 206 of the lower clamping member 136. Both urinary control devices 10, 110 operate in the same manner. Thus, in operation, the device 10, 110 is opened, as shown in FIG. 8A, and the penis 12, preferably in a flaccid state, is loaded into the device 10, 110 as shown in FIG. 8B. More specifically, with the thumb and forefinger, the user pulls and elongates the penis 12 and inserts the penis 12 between the upper clamping member 34, 134 and the lower clamping member 36, 136 such that the protrusion 98 or removable pressure mechanism 212 is disposed generally opposite the urethra 22. Then, the user closes the device 10, 110, as shown in FIG. 8C. Simultaneously, the user adjustably locks the male member 76 and the female member 78 of the self-locking mechanism 40, 140 together, as shown in FIG. 8D, thereby mounting the device 10, 110 to the penis 12 such that the penis 12 becomes immobile in the device 10, 110 in a non-painful manner and makes certain that the protrusion 98 or removable pressure mechanism 212 is disposed directly opposite the urethra 22. Preferably, the device 10, 110 is positioned approximately one-half of an inch from the head 14 of the penis 12.

When bladder pressure becomes uncomfortable, the user pulls out the penis 12 by grasping the device 10, 110 and, with the same hand, activates the release-lock button 96, which disengages the upper clamping member 34, 134 from the lower clamping member 36, 136 for immediate urination to take place. After emptying the bladder, the user repeats the above loading steps and resumes his normal activities. To deliver a different pressure to the urethra 22, the user either removes the pressure mechanism 212 from the aperture 206 and replaces it with one having a correspondingly sized upper portion 222 or replaces the device 10 with one having a correspondingly sized protrusion 98.

As can easily be seen, the device 110 allows for delivery of different pressures to the urethra 22 as a function of various sizes of penises 12 in a flaccid state. More specifically, the device 110 is selectively and variably adjustable to enable application of different pressures to the urethra 22 to accommodate needs of individual users. The device 10, 110 operatively permits blood flow through the penis 12 while preventing or substantially reducing leakage of urine from the urethra 22. At the same time, the device 10, 110 is easy to attach to, remove from, and use on the penis 12 and comfortably worn by a user. More specifically, the self-locking mechanism 40, 140 facilitates one-handed operation, easy proper positioning on the shaft 16 of the penis 12, removal for urination, and variable adjustment to enable application of different pressures to accommodate needs of individual users. Also, in operating the device 10, 110, the user does not experience pain, trauma, and/or damage to the skin and underlying tissues of the shaft 16 of the penis 12. Such ease and comfort give the user more confidence. The device 10, 110 is also lightweight, compact in design, and unobtrusive, thereby giving the user freedom of movement. The device 10, 110 is also simple to construct, dishwasher-safe, and, as a result, sanitary.

The present invention has been described in an illustrative manner. It is to be understood that the terminology that has been used is intended to be in the nature of words of description rather than of limitation. Many modifications and variations of the present invention are possible in light of the above teachings. Therefore, within the scope of the appended claims, the present invention may be practiced other than as specifically described.

What is claimed is:

1. A urinary-control device for inhibiting male incontinence, said device comprising:

an upper clamping member having first and second distal ends and a substantially arcuate inner surface extending therebetween, said inner surface adapted to be disposed about a portion of a penis;

a lower clamping member having first and second distal ends and a substantially arcuate inner surface extending therebetween, said inner surface adapted to be disposed about a portion of the penis and opposite said upper clamping member;

a hinge defined at said first distal ends of said upper and lower clamping members for allowing articulated movement of said upper and lower clamping members relative to one another; and a release mechanism defined at said second distal ends of said upper and lower clamping members opposite said hinge and adapted to adjustably lock said second distal ends together, thereby mounting said device to the penis;

said lower clamping member including a removable pressure mechanism mounted on said inner surface of said lower clamping member and between said distal ends thereof so as to be located generally opposite the urethra of the penis, said removable pressure mechanism extending in a direction toward said inner surface of said upper clamping member so as to collapse the urethra in such a manner as to inhibit flow of urine therethrough when said device is mounted to the penis, wherein said lower clamping member further includes at least one slot formed therein and said removable pressure mechanism includes a body and at least one leg extending from said body and adapted to be received in corresponding said at least one slot in snap-fit fashion.

2. A urinary-control device as set forth in claim 1, wherein said at least one slot includes a pair of slots and said at least one leg includes a pair of legs extending in cantilevered fashion from said body, each of said pair of legs adapted to be received in a corresponding one of said pair of slots.

3. A urinary-control device as set forth in claim 1, wherein said body includes an upper portion having a protrusion adapted to be located generally opposite the urethra and extending in a direction toward said inner surface of said upper clamping member so as to collapse the urethra in such a manner as to inhibit flow of urine therethrough when said device is mounted to the penis.

4. A urinary-control device as set forth in claim 1, wherein said upper clamping member includes at least one vein-relief portion formed on said inner surface of said upper clamping member and located so as to be disposed opposite the neurovascular bundle of veins in the penis such that said device does not constrict blood flow through the neurovascular bundle of veins when said device is mounted to the penis.

5. A urinary-control device as set forth in claim 4, wherein said vein-relief portion is defined by an arcuate, shallow groove formed on said inner surface of said upper clamping member and opening in the general direction of said removable pressure mechanism formed on said inner surface of said lower clamping member, said vein-relief portion extending for the entire width of said upper clamping member.

6. A urinary-control device as set forth in claim 1, wherein said upper clamping member includes a plurality of vein-relief portions disposed spaced relative to one another and formed on said inner surface of said upper clamping member, each of said plurality of vein-relief portions being defined by an arcuate, shallow groove formed on said inner surface of said upper clamping member and opening in the general direction of said removable pressure mechanism formed on said inner surface of said lower clamping member and extending for the entire width of said upper clamping member.

7. A urinary-control device as set forth in claim 6, wherein said plurality of vein-relief portions include a pair of lateral vein-relief portions disposed spaced from one another and corresponding to the subcutaneous lateral veins extending through the penis as well as a dorsal vein-relief portion disposed between said pair of lateral vein-relief portions, said dorsal vein-relief portion corresponding to the subcutaneous dorsal vein extending through the penis.

8. A urinary-control device for inhibiting male incontinence, said device comprising:
  an upper clamping member having first and second distal ends and a substantially arcuate, inner surface extending therebetween, said inner surface adapted to be disposed about a portion of a penis;
  a lower clamping member having first and second distal ends and a substantially arcuate, inner surface extending therebetween, said inner surface adapted to be disposed about a portion of the penis and opposite said upper clamping member;
  a hinge defined at said first distal ends of said upper and lower clamping members for allowing articulated movement of said upper and lower clamping members relative to one another; and
  a releasable, self-locking mechanism defined at said second distal ends of said upper and lower clamping members opposite said hinge, said self-locking mechanism including a male member and a female member, said male member cooperatively and adjustably received within said female member and including a plurality of detents formed along the length of said male member, said female member including a latching member and a biasing member that acts to bias said latching member into engagement with at least one of said plurality of detents to allow said upper and lower clamping members to be adjustably mounted to the penis, wherein said latching member includes a pair of distal ends and a pawl portion formed proximate one of said pair of distal ends, said biasing member acting on said latching member proximate said distal end that is disposed spaced from said pawl portion;
  said lower clamping member including a removable pressure mechanism mounted on said inner surface of said lower clamping member and between said distal ends thereof so as to be located generally opposite the urethra of the penis, said removable pressure mechanism extending in a direction toward said inner surface of said upper clamping member so as to collapse the urethra in such a manner as to inhibit flow of urine therethrough when said device is mounted to the penis.

9. A urinary-control device as set forth in claim 8, wherein said male member is formed on said upper clamping member and said female member is formed on said lower clamping member, said latching member being pivotable about a point disposed between said pawl portion and said biasing member in response to a force acting in a direction opposite a biasing force generated by said biasing member to pivot said pawl portion out of engagement with said at least one of said plurality of detents.

10. A urinary-control device as set forth in claim 8, wherein said upper clamping member includes at least one vein-relief portion formed on said inner surface of said upper clamping member and located so as to be disposed opposite the neurovascular bundle of veins in the penis such that said device does not constrict blood flow through the neurovascular bundle of veins when said device is mounted to the penis.

11. A urinary-control device as set forth in claim 10, wherein said upper clamping member includes a plurality of vein-relief portions disposed spaced relative to one another and formed on said inner surface of said upper clamping member, each of said plurality of vein-relief portions being defined by an arcuate, shallow groove formed on said inner surface of said upper clamping member and opening in the general direction of said removable pressure mechanism formed on said inner surface of said lower clamping member and extending for the entire width of said upper clamping member.

12. A urinary-control device as set forth in claim 11, wherein said plurality of vein-relief portions include a pair of lateral vein-relief portions disposed spaced from one another and corresponding to the subcutaneous lateral veins extending through the penis as well as a dorsal vein-relief portion disposed between said pair of lateral vein-relief portions, said dorsal vein-relief portion corresponding to the subcutaneous dorsal vein extending through the penis.

* * * * *